(12) United States Patent
Logan et al.

(10) Patent No.: US 6,505,349 B1
(45) Date of Patent: Jan. 14, 2003

(54) THERAPEUTIC GLOVE SYSTEM

(76) Inventors: Janice C. Logan, 742 Hanover St., Aurora, CO (US) 80010; Cynthia A. Pruitt, 742 Hanover St., Aurora, CO (US) 80010

( * ) Notice: Subject to any disclaimer, the term of this patent is extended or adjusted under 35 U.S.C. 154(b) by 0 days.

(21) Appl. No.: 09/928,085

(22) Filed: Aug. 10, 2001

(51) Int. Cl.[7] ............................................... A41D 19/00
(52) U.S. Cl. ........................................ 2/158; 607/114
(58) Field of Search ............................ 2/158, 159, 160, 2/161.1, 247, 20; 602/14, 21, 62; 607/111, 108, 114

(56) References Cited

U.S. PATENT DOCUMENTS

| | | | |
|---|---|---|---|
| 4,587,672 A | * | 5/1986 | Madnick et al. ............... 2/158 |
| 4,700,405 A | * | 10/1987 | Sternberg .................. 2/161.1 |
| 4,850,341 A | | 7/1989 | Fabry et al. |
| 5,014,689 A | | 5/1991 | Meunchen et al. |
| 5,214,799 A | | 6/1993 | Fabry |
| 5,305,471 A | * | 4/1994 | Steele et al. .................... 2/102 |
| D349,364 S | | 8/1994 | Rasmussen |
| 5,369,807 A | | 12/1994 | Cho et al. |
| 5,376,066 A | | 12/1994 | Phillips et al. |
| 5,415,624 A | * | 5/1995 | Williams ...................... 602/14 |
| 6,141,801 A | * | 11/2000 | Helenick ........................ 2/159 |

* cited by examiner

*Primary Examiner*—John J. Calvert
*Assistant Examiner*—Tejash Patel

(57) ABSTRACT

A therapeutic glove system for treating an injured hand and wrist of a user. The therapeutic glove system includes a glove for positioning on a hand of a user. At least one pocket is mounted on the glove. The pocket includes an opening extending into an interior of the pocket. At least one pack is provided for removably inserting in the opening in the pocket. The pack includes a temperature-retentive material for regulating a temperature of a portion of a user's hand in the glove positioned adjacent to the pocket.

19 Claims, 3 Drawing Sheets

THERAPEUTIC GLOVE SYSTEM

BACKGROUND OF THE INVENTION

1. Field of the Invention

The present invention relates to therapy gloves and more particularly pertains to a new therapeutic glove system for treating an injured hand and wrist of a user.

2. Description of the Prior Art

The use of therapy gloves is known in the prior art. More specifically, therapy gloves heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 4,850,341; 5,214,799; 5,369,807; 5,376,066; 349,364; and 5,014,689.

While these devices fulfill their respective, particular objectives and requirements, the aforementioned patents do not disclose a new therapeutic glove system. The inventive device includes a glove for positioning on a hand of a user. At least one pocket is mounted on the glove. The pocket includes an opening extending into an interior of the pocket. At least one pack is provided for removably inserting in the opening in the pocket. The pack includes a temperature-retentive material for regulating a temperature of a portion of a user's hand in the glove positioned adjacent to the pocket.

In these respects, the therapeutic glove system according to the present invention substantially departs from the conventional concepts and designs of the prior art, and in so doing provides an apparatus primarily developed for the purpose of treating an injured hand and wrist of a user.

SUMMARY OF THE INVENTION

In view of the foregoing disadvantages inherent in the known types of therapy gloves now present in the prior art, the present invention provides a new therapeutic glove system construction wherein the same can be utilized for treating an injured hand and wrist of a user.

The general purpose of the present invention, which will be described subsequently in greater detail, is to provide a new therapeutic glove system apparatus and method which has many of the advantages of the therapy gloves mentioned heretofore and many novel features that result in a new therapeutic glove system which is not anticipated, rendered obvious, suggested, or even implied by any of the prior art therapy gloves, either alone or in any combination thereof.

To attain this, the present invention generally comprises a glove for positioning on a hand of a user. At least one pocket is mounted on the glove. The pocket includes an opening extending into an interior of the pocket. At least one pack is provided for removably inserting in the opening in the pocket. The pack includes a temperature-retentive material for regulating a temperature of a portion of a user's hand in the glove positioned adjacent to the pocket.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new therapeutic glove system apparatus and method which has many of the advantages of the therapy gloves mentioned heretofore and many novel features that result in a new therapeutic glove system which is not anticipated, rendered obvious, suggested, or even implied by any of the prior art therapy gloves, either alone or in any combination thereof.

It is another object of the present invention to provide a new therapeutic glove system which may be easily and efficiently manufactured and marketed.

It is a further object of the present invention to provide a new therapeutic glove system which is of a durable and reliable construction.

An even further object of the present invention is to provide a new therapeutic glove system which is susceptible of a low cost of manufacture with regard to both materials and labor, and which accordingly is then susceptible of low prices of sale to the consuming public, thereby making such therapeutic glove system economically available to the buying public.

Still yet another object of the present invention is to provide a new therapeutic glove system which provides in the apparatuses and methods of the prior art some of the advantages thereof, while simultaneously overcoming some of the disadvantages normally associated therewith.

Still another object of the present invention is to provide a new therapeutic glove system for treating an injured hand and wrist of a user.

Yet another object of the present invention is to provide a new therapeutic glove system which includes a glove for positioning on a hand of a user. At least one pocket is mounted on the glove. The pocket includes an opening extending into an interior of the pocket. At least one pack is provided for removably inserting in the opening in the pocket. The pack includes a temperature-retentive material for regulating a temperature of a portion of a user's hand in the glove positioned adjacent to the pocket.

Still yet another object of the present invention is to provide a new therapeutic glove system that provides a user relief from hand and wrist pain due to carpal tunnel and hand and wrist injuries.

Even still another object of the present invention is to provide a new therapeutic glove system that is, unlike the prior art, may be used on either hand requiring a user to only purchase a single glove.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
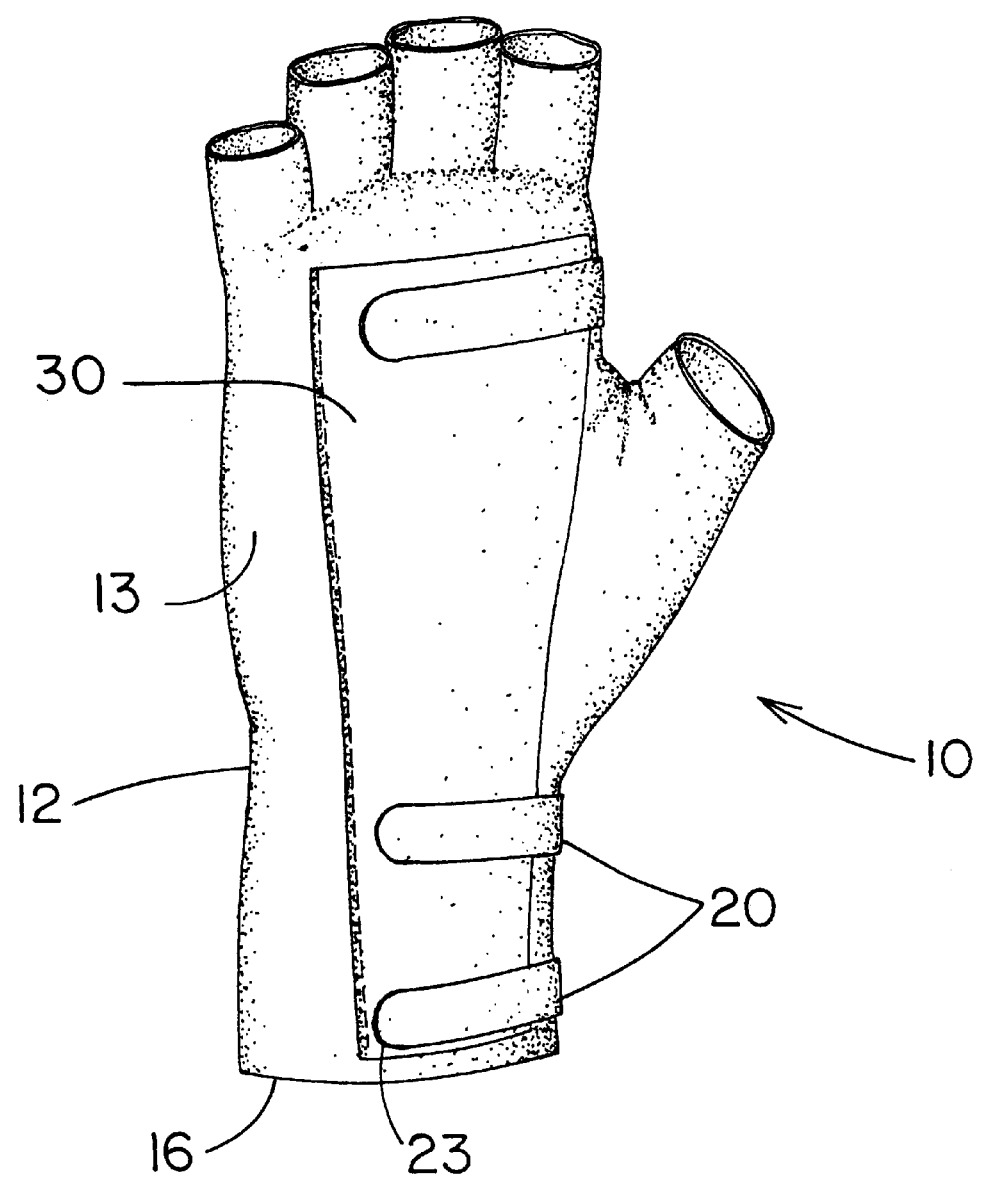
FIG. 1 is a schematic perspective view of a new therapeutic glove system according to the present invention.
Figure 2:
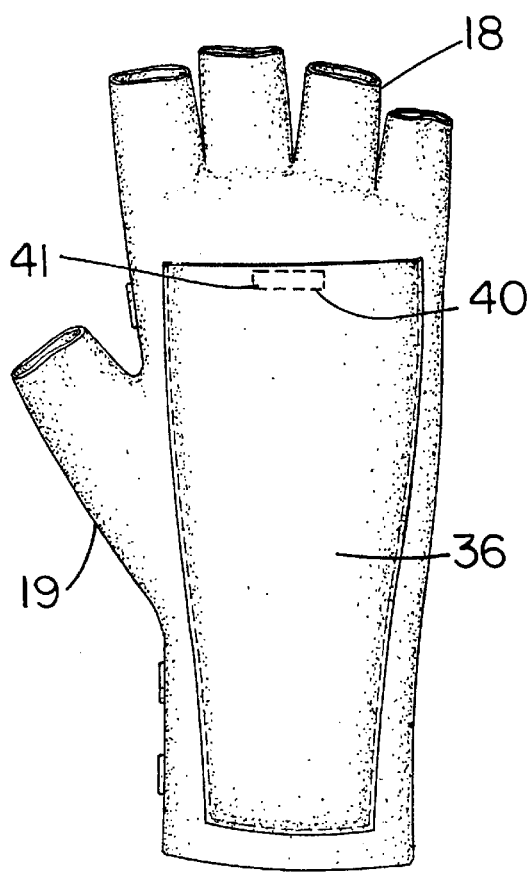
FIG. 2 is a schematic frontal view of the present invention.
Figure 3:
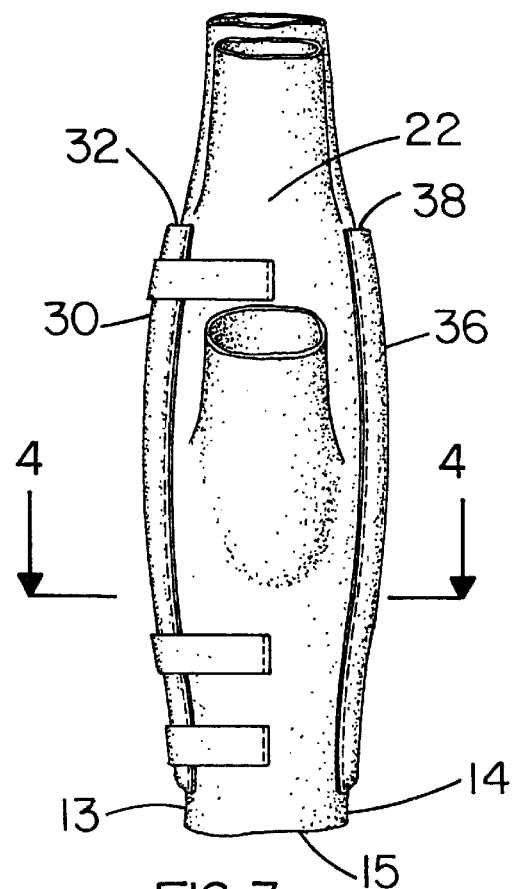
FIG. 3 is a schematic side view of the present invention.
Figure 4:
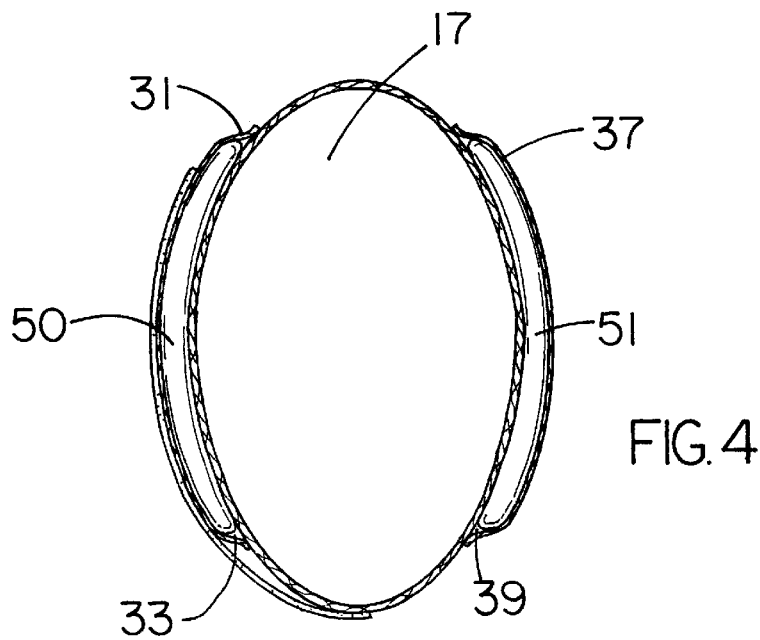
FIG. 4 is a schematic cross-sectional view of the present invention taken along line 4—4 of FIG. 3.
Figure 5:
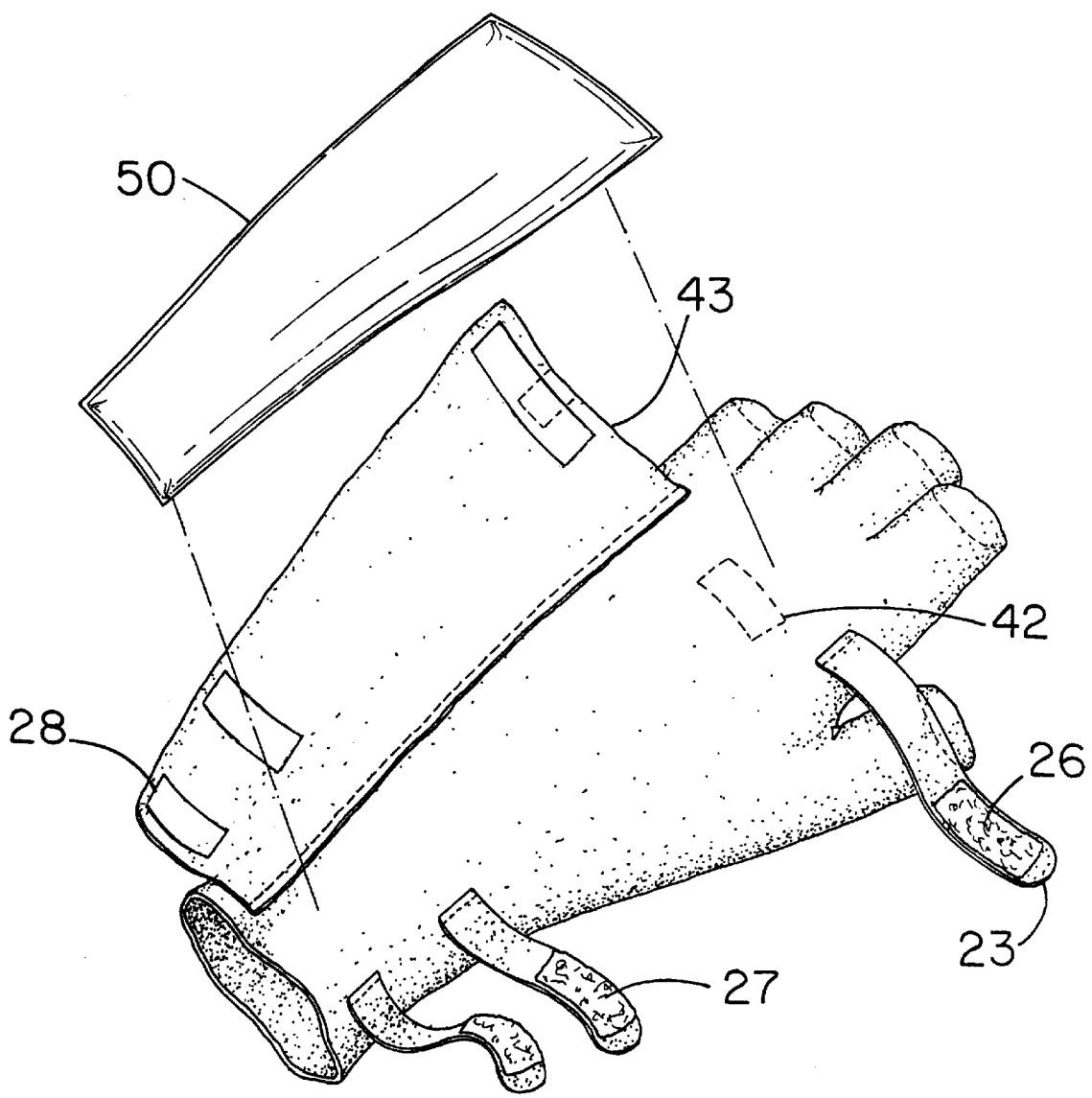
FIG. 5 is a schematic exploded view of the present invention.

With reference now to the drawings, and in particular to FIGS. 1 through 5 thereof, a new therapeutic glove system embodying the principles and concepts of the present invention and generally designated by the reference numeral 10 will be described.

As best illustrated in FIGS. 1 through 5, the therapeutic glove system 10 generally comprises a glove 12 for positioning on a hand of a user. The glove 12 includes a first surface 13 and a second surface 14. An end 15 of the glove 12 includes an opening 16 extending into an interior 17 of the glove 12 for selectively receiving a left or right hand of a user. The glove 12 may include a plurality of finger portions 18 and a thumb portion 19 for selectively receiving fingers and thumb of a user. The glove 12 may comprise a resiliently flexible material such as, for example, a nylon material.

A plurality of straps 20 may be provided for selectively restricting a volume of the interior 17 of the glove 12. Each of the straps 20 may be mounted on a lateral surface 22 of the glove 12. An end 23 of each of the straps 20 may be releasably coupled to the first surface 13 of the glove 12. Each of the straps 20 may comprise a resiliently flexible material such as, for example, a nylon material.

A securing means 26 may be provided for securing the end 23 of each of the straps 20 to the glove 12. The securing means 26 may comprise a first securing portion 27 and a second securing portion 28. The first securing portion 27 may be mounted on the end 23 of each of the straps 20. The second securing portion 28 may be mounted on a portion of the glove 12. The first 27 and second 28 securing portions are preferably releasably coupled together. The securing means 26 may comprise a hook and loop fastener, however, other types of securing means may be employed.

A first pocket 30 is mounted on the first surface 13 of the glove 12. The first pocket 30 includes a pocket panel 31 coupled to the front surface 13 of the glove 12. The first pocket 30 includes an opening 32 extending into an interior 33 of the first pocket 30. The first pocket 30 includes a longitudinal axis extending between the finger portions 18 and the opening 16 in the glove 12, orientated generally parallel to a longitudinal axis of the glove 12. The opening 32 of the first pocket 30 may be positioned generally adjacent to the finger portions 18 of the glove 12. The first pocket 30 may comprise a resiliently flexible material such as, for example, a nylon material. The ends 23 of each of the straps 20 may be coupled to the pocket panel 31.

A second pocket 36 may be mounted on the second surface 14 of the glove 14. The second pocket 36 includes a pocket panel 37 coupled to the second surface 14 of the glove 12. The second pocket includes an opening 38 extending into an interior 39 of the second pocket 36. The second pocket 36 includes a longitudinal axis orientated generally parallel to the longitudinal axis of the glove 12. The opening 38 of the second pocket 36 may be positioned generally adjacent to the finger portions 18 of the glove 12. The second pocket 36 may comprise a resiliently flexible material such as, for example, a nylon material.

A fastening means 40 may be provided that is designed for closing the openings 32 and 38 in the first 30 and second 36 pockets. The fastening means 40 may include a first fastening portion 41 and a second fastening portion 42. The first fastening portion 41 may be mounted on an inner surface 43 of each of the pocket panels 31 and 37. The second fastening portion 42 may be mounted on the first 13 and second 14 surfaces of the glove 12. The first 41 and second 42 fastening portions are preferably releasably coupled together.

A first pack 50 is provided for removably inserting in the opening 32 or 38 in one of the pockets 30 and 36. The first pack 50 may be designed for heating a hand of a user in the glove 12. A second pack 51 may be provided that is removably insertable in the opening 32 or 38 in one of the pockets 30 and 36. The second pack 51 may be designed for cooling a hand of a user in the glove 12. The first 50 and second 51 packs may employ a temperature-retentive material that is pliable for forming to the hand of the user. A single pack may be employed that has both heating and cooling characteristics.

In use, the first 50 and second 51 packs may be placed in a refrigerator to be cooled or a microwave to be heated. Once the first 50 and second 51 packs are cooled or heated they may be placed into one of the pockets 30 and 36 to regulate a temperature of the user's hand.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A therapeutic glove system for treating an injured hand and wrist of a user, said system comprising:
   a glove for positioning on a hand of a user;
   at least one pocket being mounted on said glove, said pocket having an opening extending into an interior of said pocket;
   at least one pack for removably positioning in said pocket, said pack comprising a temperature-retentive material for regulating a temperature of a portion of the user's hand in said glove positioned adjacent to said pocket;
   wherein an end of said glove has an opening extending into an interior of said glove for selectively receiving a left or right hand of a user;
   wherein said glove has a plurality of finger portions and a thumb portion for selectively receiving fingers and thumb of a user, said at least one pocket extending generally between said finger portions and said opening;
   a plurality of straps being mounted on said glove for selectively restricting a volume of said interior of said glove;
   wherein said pocket includes a pocket panel being coupled to an exterior surface of said glove; and
   a fastening means being adapted for closing said opening in said pocket, said fastening means being mounted on said glove.

2. The therapeutic glove system of claim 1, wherein said fastening means includes a first fastening portion and a second fastening portion, said first fastening portion being mounted on an inner surface of said pocket panel, said second fastening portion being mounted on said exterior surface of said glove, said first and second fastening portions being releasably coupled together.

3. The therapeutic glove system of claim 1, wherein said at least one pocket comprises a first pocket and a second pocket, each of said pockets being mounted on said glove, said first pocket being mounted on said exterior surface of said glove, said second pocket being mounted on an interior surface of said glove.

4. The therapeutic glove system of claim 3, wherein said second pocket has a pocket panel being coupled to said interior surface of said glove; and
   wherein said second pocket has an opening extending into an interior of said second pocket.

5. The therapeutic glove system of claim 4, wherein said at least one pack comprises a first pack and a second pack, said first pack being removably insertable in said opening in said first pocket, said second pack being removably insertable in said opening in said second pocket.

6. A therapeutic glove system for treating an injured hand and wrist of a user, said system comprising:
   a glove for positioning on a hand of a user;
   at least one pocket being mounted on an exterior surface of said glove, said pocket having an opening extending into an interior of said pocket;
   at least one pack for removably inserting in said opening in said pocket, said pack including a temperature-retentive material for regulating a temperature of a portion of a user's hand in said glove positioned adjacent to said pocket;
   wherein an end of said glove has an opening extending into an interior of said glove for selectively receiving a left or right hand of a user; and
   additionally including a plurality of straps mounted on said glove for selectively restricting a volume of said interior of said glove.

7. The therapeutic glove system of claim 4, wherein each of said straps is mounted on a lateral surface of said glove, an end of each of said straps being releasably coupled to said first surface of said glove;
   a securing means for securing said end of each of said straps to said glove; and
   wherein said securing means comprises a first securing portion and a second securing portion, said first securing portion being mounted on said end of each of said straps, said second securing portion being mounted on said glove, said first and second securing portions being releasably coupled together.

8. The therapeutic glove system of claim 6, wherein said glove has a plurality of finger portions and a thumb portion for selectively receiving fingers and thumb of a user, said at least one pocket extending generally between said finger portions and said opening.

9. The therapeutic glove system of claim 6, wherein each of said straps is mounted on a lateral surface of said glove, an end of each of said straps being releasably coupled to said first surface of said glove.

10. The therapeutic glove system of claim 9, additionally including a securing means for securing said end of each of said straps to said glove.

11. The therapeutic glove system of claim 10, wherein said securing means comprises a first securing portion and a second securing portion, said first securing portion being mounted on said end of each of said straps, said second securing portion being mounted on said glove, said first and second securing portions being releasably couplable together.

12. The therapeutic glove system of claim 6, wherein said pocket includes a pocket panel being coupled to said exterior surface of said glove.

13. The therapeutic glove system of claim 12, additionally including a fastening means adapted for closing said opening in said pocket, said fastening means being mounted on said glove.

14. The therapeutic glove system of claim 13, wherein said fastening means includes a first fastening portion and a second fastening portion, said first fastening portion being mounted on an inner surface of said pocket panel, said second fastening portion being mounted on said exterior surface of said glove, said first and second fastening portions being releasably couplable together.

15. The therapeutic glove system of claim 6, wherein said at least one pocket comprises a first pocket and a second pocket, each of said pockets being mounted on said glove, said first pocket being mounted on said first surface of said glove, said second pocket being mounted on a second surface of said glove.

16. The therapeutic glove system of claim 15, wherein said second pocket has a pocket panel being coupled to said interior surface of said glove.

17. The therapeutic glove system of claim 16, wherein said second pocket has an opening extending into an interior of said second pocket.

18. The therapeutic glove system of claim 17, wherein said at least one pack comprises a first pack and a second pack, said first pack being removably insertable in said opening in said first pocket, said second pack being removably insertable in said opening in said second pocket.

19. A therapeutic glove system for treating an injured hand and wrist of a user, said system comprising:

- a glove for positioning on a hand of a user, said glove including an exterior surface and an interior surface, an end of said glove having an opening extending into an interior of said glove for selectively receiving a left or right hand of a user, said glove having a plurality of finger portions and a thumb portion for selectively receiving fingers and thumb of a user, said glove comprising a resiliently flexible material;
- a plurality of straps for selectively restricting a volume of said interior of said glove, each of said straps being mounted on a lateral surface of said glove, an end of each of said straps being releasably coupled to said first surface of said glove;
- a securing means for securing said end of each of said straps to said glove, said securing means comprising a first securing portion and a second securing portion, said first securing portion being mounted on said end of each of said straps, said second securing portion being mounted on said glove, said first and second securing portions being releasably coupled together;
- a fastening means adapted for closing said opening in said first and second pockets, said fastening means including a first fastening portion and a second fastening portion, said first fastening portion being mounted on an inner surface of each of said pocket panels, said second fastening portion being mounted on said exterior and interior second surfaces of said glove, said first and second fastening portions being releasably coupled together;
- a first pocket being mounted on said exterior surface of said glove, said first pocket having a pocket panel being coupled to said exterior surface of said glove, said first pocket having an opening extending into an interior of said first pocket, said first pocket having a longitudinal axis orientated generally parallel to a longitudinal axis of said glove, said opening of said first pocket being positioned generally adjacent to said finger portions of said glove, said first pocket comprising a resiliently flexible material;
- a second pocket being mounted on said interior surface of said glove, said second pocket having a pocket panel being coupled to said interior surface of said glove, said second pocket having an opening extending into an interior of said second pocket, said second pocket having a longitudinal axis orientated generally parallel to a longitudinal axis of said glove, said opening of said second pocket being positioned generally adjacent to said finger portions of said glove, said second pocket comprising a resiliently flexible material;
- a first pack for removably inserting in said opening in one of said pockets, said first pack including a temperature-retentive material for heating a hand of a user in said glove;
- a second pack for removably inserting in said opening in one of said pockets, said second pack including a temperature-retentive material for cooling a hand of a user in said glove.

* * * * *